US006352831B1

(12) United States Patent
Buschard et al.

(10) Patent No.: US 6,352,831 B1
(45) Date of Patent: Mar. 5, 2002

(54) GLYCOLIPID COMPLEXES AND THEIR USES

(75) Inventors: Karsten Buschard, Charlottenlund (DK); Pam Fredman; Jan-Eric Månsson, both of Göteborg (SE)

(73) Assignee: A+ Science Invest AB, Gothenburg (SE)

( * ) Notice: Subject to any disclaimer, the term of this patent is extended or adjusted under 35 U.S.C. 154(b) by 0 days.

(21) Appl. No.: 09/180,492

(22) PCT Filed: May 10, 1997

(86) PCT No.: PCT/SE97/00769

§ 371 Date: May 12, 1999

§ 102(e) Date: May 12, 1999

(87) PCT Pub. No.: WO97/42974

PCT Pub. Date: Nov. 20, 1997

(30) Foreign Application Priority Data

May 13, 1996 (SE) ................................................ 9601817

(51) Int. Cl.[7] ..................... G01N 33/53; G01W 33/00; A61K 31/00; A61K 31/74
(52) U.S. Cl. ..................... 435/7.1; 435/7.92; 435/7.93; 435/7.95; 435/7.96; 514/866; 424/78.17; 424/78.18
(58) Field of Search .................. 435/7.1, 7.92, 435/7.93, 7.94, 7.95; 426/78.17, 78.18; 514/866

(56) References Cited

FOREIGN PATENT DOCUMENTS

| JP | 62-008055 | 1/1987 |
| WO | WO 9219633 | 11/1992 |
| WO | WO 9413311 | 6/1994 |

OTHER PUBLICATIONS

Monti et al, *Biochimica et Biophysica Acta*, 1124 (1992):80–87.
Buschard et al, *APMIS*, 101 (1993):963–970.
Fredman et al, *Biochem. J.*, 251 (1998):17–22.
Fredman et al, *J. Neurol.*, 235 (1991):75–79.
Buschard et al, *Lancet*, 342 (1993):840.
Fredman et al, *J. Neurol.*, 240 (1993):381–387.
Viani al, *Biochimica et Biophysica Acta*, 1002 (1989):20–27.

*Primary Examiner*—Mark Navarro
*Assistant Examiner*—Padma Baskar
(74) *Attorney, Agent, or Firm*—Dinsmore & Shohl LLP

(57) ABSTRACT

A complex between a water-soluble polymer containing hydrophobic regions and a glycolipid, immunoassays utilizing the complex as an immune reagent and diagnostic methods to be used in the context of neuropathy and insulin-dependent diabetes. The diagnostic methods employ anti-glycolipid antibody as a marker. The preferred glycolipid is sulfatide.

16 Claims, No Drawings

GLYCOLIPID COMPLEXES AND THEIR USES

TECHNICAL FIELD

The present invention relates to novel forms of glycolipids and novel methods for assaying anti-glycolipid antibodies. The preferred glycolipid is sulphatide. The novel assaying methods are particularly adapted for the diagnosis of any disease for which elevated levels of an anti-glycolipid autoantibody is a marker. The disease may be, for instance, neuropathy and insulin-dependent diabetes (IDDM, Type 1 diabetes) including diagnoses excluding Type 2 diabetes, late complications associated therewith and monitoring the treatment of IDDM. The novel forms of sulphatide may potentially find use as a medicament in the treatment of IDDM.

BACKGROUND OF THE INVENTION

Sulphatide, the most important antigen of the present invention is a glycosphingolipid having the structure:

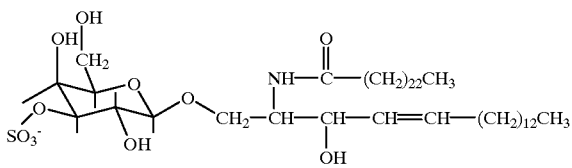

(=galactosylceramide-3-sulphate).

The development of manifested IDDM involves an autoimmune process where the insulin producing cells in the islet of Langerhan in the pancreas gradually are knocked out. At the time of diagnoses 70–80% of the cells have been destroyed and the remaining cells will generally disappear within a 5 year period. Prediabetic individuals are those which have an ongoing destruction of insulin-producing cells but still without clinical symptoms. A particular type of prediabetic individuals are non-IDDM patients whose disease will switch to IDDM.

In the context of the invention the term IDDM include manifested IDDM as well as preforms thereof, if not otherwise specified.

The main marker autoantibodies found in IDDM are islet cell antibodies (ICA), anti-glutamic acid decarboxylase antibodies (anti-GAD), anti-insulin antibodies (IAA), antibodies against 37 kD protein (likely the same as tyrosine phosphatase) and anti-sulphatide antibodies. The main disadvantages of these markers are:

ICAs are determined by conventional immunohistochemistry which make them unsuitable for large screenings. They are normally considered good predictors of IDDM but their assay suffers from relatively high intra- and interassay variations.

Anti-GAD antibodies are easy to determine also in large scale screenings, but they may not be of a strong predictive value.

IAAs are fairly easy to determine but are not present in more than 40–50% of newly diagnosed type 1 diabetic children and is less common in adult patients.

Anti-37 kD protein antibodies have a significant lower frequency (about 50%) than ICA and anti-GAD antibodies.

Both ICAs and anti-GAD antibodies have been used for the diagnoses of prediabetics.

Anti-sulphatide antibodies have been recognized as a good marker for manifested IDDM (Buschard et al., Lancet 342 (1993) page 840-; and Buschard et al., APMIS 101 (1993) 963–970). Results supporting a diagnostic link between this type of antibodies and prediabetic forms of IDDM have not hitherto been published. Increased titers of anti-sulphatide antibody have been found in neuropathy patients and could be used for identification of individuals that might develop neuropathy. Part of diabetes type 2 patients also develop neuropathy. In a preliminary study one of the present inventors has shown that diabetes type 2 patients without neuropathy did not have anti-sulphatide antibody reactivity and there is thus a possibility that those with neuropathy development will be positive and thus anti-sulphatide antibody might be useful as a prognostic tool. See Fredman et al., J. Neurolog. 238 (1991) 75–79.

Serum levels of antibodies towards glycosphingolipids have often been assayed by a combination of thin layer chromatography (TLC) of the antigens and ELISA methodology (enzyme-linked immuno sorbent assay) employing the chromatographed material as antigen for assaying occurrence of serum antibodies (TLC-ELISA) (Fredman et al., J. Neurol. 238 (1991) 75–79; and Fredman et al., J. Neurol. 240 (1993) 381–387).

The assaying methods of anti-glycolipid antibodies have been problematic, in particular the methods for anti-sulphatide antibodies.

Sulphated glycolipids, in particular sulphatide, lactosylceramide-3-sulphate and seminolipid and corresponding antibodies have been suggested as diagnostic markers and therapeutic agents in the context of diabetes (Buschard K, WO-A-9219633).

We have tried to vary the attachment of sulphatide to plastic wells, and have clear evidences that direct adsorption results in a high coefficient of variation and often gives unspecific reactions without any correlation to earlier TLC-ELISA findings. The criticality of exposing correctly both the lipid moiety and the carbohydrate moiety of short carbohydrate chain glycolipids has also been illustrated with monoclonal anti-sulphatide antibodies. Thus, the monoclonal anti-sulphatide antibody described by Fredman et al (Biochem. J. 251 (1988) 17–22) is sensitive to changes in the lipid part. Another aspect is that galactose substituted with sulphate is a common epitope on several glycoproteins and glycolipids, and there are no results so far supporting that a general reactivity towards this epitope is relevant for the development of IDDM and its late complications. Accordingly, the main problem the invention sets out to solve relates to the presentation of glycolipid epitopes.

Another problem the invention sets out to solve is connected to the diagnoses of prediabetic forms of IDDM.

SUMMARY OF THE INVENTION

A first objective of the invention is to improve the presentation of glycolipid antigens/haptens in immunoassays and potentially also in therapy. The antigens/haptens primarily concerned exhibit short carbohydrate chains.

A second objective is to provide improved immunoassays for measuring anti-glycolipid antibodies or glycolipid antigens/haptens, in particular autoantibodies against glycosphingolipid antigens exhibiting mono- and/or disaccharide units that may be sulphated.

A third objective is to provide improved diagnostic methods utilizing as markers auto-antibodies binding to one or more of the previously mentioned glycolipid antigens/haptens for diagnosing IDDM including preforms thereof.

A fourth objective is to provide diagnostic methods for determining preforms of IDDM.

These objectives may be complied with by complexing the glycolipid antigens/haptens as defined above to a polymeric hydrophilic carrier exhibiting hydrophobic regions. Examples of suitable carrier molecules are delipidized forms of hydrophilic proteins, such as albumin, that are capable of associating to lipid compounds, such as fatty acids and derivatives thereof.

DETAILED DESCRIPTION

Accordingly a first aspect of the invention is a complex between a water-soluble carrier polymer and a glycolipid antigen, preferably a glycosphingolipid antigen, that exhibits a mono- or disaccharide unit that may or may not be sulphated in the 3-position of its terminal carbohydrate unit. The water-soluble polymer is preferably a delipidized form of a protein that have hydrophobic regions that are capable of binding to lipids, such as fatty acids. At the priority date the most preferred water-soluble polymer was delipidized albumin. The water-soluble polymer may be insolubilized by covalent attachment or physical adsorption to any of the known solid phases used in immunoassays or chromatography. Insolubilization may be carried out either before or after complex formation with the glycolipid antigen/hapten concerned. In this aspect of the invention the best mode encompasses sulphatide as the glycolipid antigen/ hapten. The forces keeping the glycolipid antigen/hapten complexed is believed to be mainly hydrophobic, meaning that at the priority the preferred variant of the inventive complex is thought to be a non-covalently associated complex between the carrier polymer and the glycolipid.

A second aspect of the invention is an immunoassay for anti-glycolipid antibodies or glycolipid antigen/hapten utilizing the above-mentioned glycolipid complex as an antigen. In this type of assays, an immune complex is formed between the inventive type of glycolipid-carrier polymer complex and the appropriate anti-glycolipid antibody (analyte) of a sample in an amount that is related, either qualitatively or quantitatively, to the amount of anti-glycolipid antibody in the sample. In an alternative embodiment the glycolipid antigen/hapten is the analyte which is allowed to compete with the glycolipid-carrier polymer complex as defined above for binding to an added anti-glycolipid antibody. In order to facilitate measurement, further reactants that are capable of being incorporated into the immune complex may be included, e.g. labelled reactants (labelled antibodies or labelled antigens) or insoluble or insolubilizable reactants. Examples of labels that can be used are enzymes, enzyme substrates, cofactors, coenzymes, fluorophores, dyes, particles such as latex particles, carbon particles, metal particles, radioactive isotopes etc. The labelled reactant is used in an amount so that the amount incorporated and/or not incorporated into the (glycolipid) - - - (anti-glycolipid antibody) complex becomes a measure of the level of analyte in the sample. In case the signal from the label changes upon being incorporated into the immune complex, no physical separation of complex-bound from non-complex-bound form of the label is necessary before measuring the signal from the label. In case complex formation does not lead to any signal change, physical separation of complex-bound from non-complex-bound form of the label becomes imperative. In case separation is accomplished one speaks about heterogeneous assays while otherwise the assays are called homogeneous. Physical separation of label not incorporated into the immune complex from label incorporated into the immune complex is normally accomplished by utilizing a reactant that is insoluble or insolubilizable in the assay medium.

Other ways of subdividing immunoassays are in competitive and non-competitive assays (sandwich). Still other types are agglutination assays, turbidometric assays, precipitation assays that may or may not be homogeneous/heterogeneous and/or competitive/non-competitive etc.

The normal conditions for immune assays are applicable, which means that the pH during immune reactions normally is within the range 4–11, the temperature between 0–35° C. etc. For heterogeneous assays, each of the various antigen-antibody reactions contemplated are normally followed by intermediate separation and washing steps to remove non-specifically bound immune reactants and other disturbing substances. The medium for the reactions is normally water (aqueous) buffered to the appropriate pH.

The sample used derives from a body fluid and may be a blood sample such as whole blood, serum or plasma, or any other type of sample that may contain the anti-glycolipid antibody or glycolipid antigen/hapten concerned (urine, cerebrospinal fluid, lacrymal fluid, saliva etc.)

The immunoassays of this aspect of the invention may be used either for diagnoses or in order to screen for or characterize monoclonal antibodies directed towards glycolipid antigens of the above-mentioned type.

As per the priority date the most preferred mode of the second aspect of the invention is given in the experimental part and encompasses delipidized albumin as the carrier polymer fixed to a solid phase and sulphatide as the glycolipid. The assay protocol encompasses a three layered sandwich assay in which the sample is incubated with the carrier polymer which subsequently is incubated with labelled anti-human antibody to the formation of the insolubilized ternary immune complex: glycolipid - - - anti-glycolipid antibody - - - labelled anti-antibody.

The third aspect of the invention is a method for diagnosing disorders related to an elevated level of anti-glycolipid antigen/hapten antibody as defined above by utilizing an immunoassay of the above-mentioned type. With respect to anti-sulphatide antibodies the method may be applied in the context of diagnosing neuropathy or IDDM including prediabetic forms thereof and monitoring of treatment regimens, such as prophylactic treatment e.g. with insulin. Uses included are differential diagnoses of IDDM/non-IDDM and/or diagnoses/prediction of diabetic late complications (neuropathy, retinopathy, and neuropathy) and/or monitoring of treatment regimens in general. A potential important diagnostic use included is the determination of preforms of IDDM in non-IDDM individuals.

A fourth aspect of the invention relates particularly to the diagnoses of prediabetic forms of IDDM utilizing elevated sample levels of anti-sulphatide antibody as a marker for a prediabetic state in the patient from which the sample derives. In this aspect any type of assay, particularly immunoassays, may be used, although the best results will, with the present knowledge, be obtained in case the assay is run in accordance with the above-mentioned third aspect with anti-sulphatide antibody as the analyte.

It has been realized during the development of the present invention that the diagnostic use of the inventive immunoassay method for elevated levels of anti-sulphatide antibody may be further improved in case it also takes into account elevated levels of other marker autoantibodies found in the context of IDDM as described above, for instance islet cell antibodies (ICA), anti-glutamic acid decarboxylase antibodies (anti-GAD), anti-insulin antibodies (IAA), antibodies against 37 kD protein (likely the same as tyrosine phosphatase). It is believed that in particular a simultaneous finding of elevated levels of anti-sulphatide antibody and anti-GAD improves the diagnostic value by increasing the specificity.

A potent fifth aspect of the invention, is to use the complex defined in the context of the first aspect of the invention as the active ingredient/drug in pharmaceutical compositions. The preferred mode includes the above-mentioned novel sulphatide complexes to prevent and/or delay development of diabetes (IDDM) and to the treatment of diseases related to late complications of diabetes (IDDM). The complexes concerned may, for example, interact with the immunological ligand and/or immune active cells involved in the pathogenic process and thereby inhibit their binding to glycolipid/sulphatide in target cells like α- and β-cells of the pancreas. Potentially the glycolipid complexes of the first aspect of the invention may also interact pharmacologically in intracellular events involved in the disease process and caused by sulphatide and/or its metabolic products. In particular sulphatide complexes as defined above may be used as vaccines in order to prevent, delay or alter IDDM or its late complications.

During the priority year it has been realized that diagnoses in the context of IDDM by assaying for anti-sulphatide antibodies may be further improved in case one also accounts for elevated levels of anti-GAD antibody. The improvement mainly relates to an increased in the specificity. This type of diagnoses is not linked to any specific method for assaying anti-sulphatide or anti-GAD antibodies, although at the filing date it was preferred to utilize the novel forms of glycolipids as described for assaying anti-sulphatide antibody. Employment of elevated levels of both anti-sulphatide and anti-GAD antibodies in combination as markers in the context of IDDM as described above is a separate invention.

EXPERIMENTAL PART

Production of Delipidizid Albumin

Albumin was delipidized with hexane containing 5% glacial acetic acid, at +4° C. After thorough washing with hexane the albumin was dialyzed against Milli Q-water and lyophilized.

Biotinylated Delipidized Albumin

Fatty acid free albumin as described above was dissolved in 0.1 M $NaHCO_3$ to a concentration of 10 g/L. Biotin-N-hydroxy succinimide, 0.1 M in dimethyl formamide, was added to a final concentration of 0.02 M. The final mixture was left at 20° C. for 60 min and an equal volume of phosphate buffered saline (PBS) was added. The reaction product was dialysed against 5 changes of PBS at +4° C. for 24 hs.

Preparation of Sulphatide

Bovine brain was homogenized with an equal volume of water. Methanol and chloroform were then added to a final ratio of 4:8:3 (by volume, chloroform-methanol-water). The lipid extract obtained was freed from particles by centrifugation. Low molecular weight components were removed by partition after addition of chloroform and methanol to a ratio of 4:2:1 (by volume, chloroform-methanol-water). The crude lipid extract was chromatographed on silica gel. The isolated sulphatide fraction was saponified and rechromatographed on silica gel. After repeated partition the sulphatide fraction was further purified by ion-exchange chromatography. Finally the purified fraction was dissolved in methanol and precipitated by addition of acetone. The isolated sulphatide fraction was characterized by mass spectrometry (FAB-MS). The recovery was about 1.5 g sulphatide per kg of bovine brain.

Adsorption of Sulphatide to Albumin

Sulphatide (100 nmole in chloroform-methanol-water mixture was evaporated to dryness and redissolved in 500 μl sodium acetate (0.05 M pH 4.5) and sonicated for 15 min at room temperature. To this solution was added 0,5 mL delipidized albumin dissolved in the same buffer (2 mg/mL). The mixture was incubated over night at room temperature under careful mixing. Thereafter the albumin with sulphatide adsorbed was precipitated by the addition of 50 μL of 10% TCA (trichloro acetic acid) in water at +4° C. After 30 min at +4° C. the mixture was centrifuged (+4° C.) at 23,000×g for 3 min. The pellet was suspended in 1 mL PBS and kept at +4° C. The procedure could also be applied to biotinylated albumin.

Binding Sulphatide-albumin to a Solid Phase

Sulphatide-albumin was suspended in 50 mM carbonate buffer pH 9.6 to a concentration of 2.5 mmole/mL and 100 μL of this solution was added to the wells of a microtiter plate (Nunc Storwell Maxisorp immunomoduler, Denmark). The plate was incubated for more than 2 hours at 37° C. and was then sealed with parafilm and kept at +4° C. until used. Just prior to the assay, the coating solution was flicked out and the wells incubated with 100 μL of PBS containing 1% dry milk powder (w/v) for one hour in order to block the surface for unspecific binding. The procedure could be applied also to sulphatide bound to biotinylated albumin.

Assay Protocol

Serum samples, 50 μL of serum diluted 1:400 with PBS containing 1% milk powder were added to the wells of a microtiter plate treated as described above. In case of high sulphatide titer sera, the samples were further diluted. The plates were then incubated at +4° C. over night. A pool of sera from blood donors (50 serum samples each individually found to be negative for anti-sulphatide reactivity analysed with TLC-ELISA) was used as reference. A positive serum was used as an internal standard. Each sample was analysed in triplicate. After incubation the samples were flicked out and the wells washed with NUNC immunowasher 6 times with 0.1% albumin dissolved in PBS. Thereafter 50 μL phosphatase conjugated anti-human IgG (Zymed, BioZac, Sweden) diluted 1:500 with 1% albumin in PBS were added and the plate incubated for 1 hour at room temperature. Unbound components was then removed by washing 5 times with PBS containing albumin (1%). Thereafter incubation was performed at +37° C. with 100 μL p-nitro phenyl phosphate (1 mg/mL) (phosphatase-substrate tablets 104, Sigma, U.S.A.) dissolved in 1.0 M diethanol amine buffer pH 9.8. The enzymatic reaction was stopped by adding 50 μL 3 M NaOH. The absorbance was the read at 405 nm.

The results on clinical samples have indicated safer diagnoses in the context of IDDM, and have also showed, for the first time, that elevated levels of anti-sulphatide antibody functions as a marker for preforms of IDDM. In addition the usefulness of anti-sulphatide antibody as a marker for monitoring treatment regimens, the results suggested diagnoses/prediction of diabetic late complications with this antibody as a marker.

We claim:

1. A method for assaying for an anti-glycolipid antibody comprising contacting a sample containing the anti-glycolipid antibody with a complex of a water soluble polymer containing hydrophobic regions and the glycolipid.

2. The immunoassay method of claim 1, wherein the polymer and the glycolipid are non-covalently bound to each other.

3. The immunoassay method of claim 1, wherein the water-soluble polymer is a a delipidized protein that in native form binds lipids.

4. The immunoassay method of claim 1, wherein the glycolipid is a glycosphingolipid.

5. The immunoassay method of claim 1, wherein the glycolipid contains one mono- or disaccharide unit.

6. The immunoassay method of claim 1, wherein the glycolipid is sulphatide.

7. The immunoassay method of claim 1, wherein the water-soluble polymer is albumin.

8. A method for assaying for a glycolipid, comprising contacting a sample containing the glycolipid with anti-glycolipid antibodies and with a complex of a water soluble polymer containing hydrophobic regions and the glycolipid.

9. The immunoassay method of claim 8, wherein the polymer and glycolipid are non-covalently bound to each other.

10. The immunoassay method of claim 8, wherein the water-soluble polymer is a delipidized protein that in native form binds lipids.

11. The immunoassay method of claim 8, wherein the glycolipid is a glycosphingolipid.

12. The immunoassay method of claim 8, wherein the glycolipid contains one mono- or disaccharide unit.

13. The immunoassay method of claim 8, wherein the glycolipid is sulphatide.

14. The immunoassay method of claim 8, wherein the water-soluble polymer is albumin.

15. A method of diagnosis of neuropathy or insulin-dependent diabetes mellitus (IDDM), comprising assaying for anti-sulphatide antibody by contacting a sample with a complex of a water-soluble polymer containing hydrophobic regions and sulphatide, wherein presence of anti-sulphatide antibody indicates neuropathy or insulin-dependent diabetes mellitus.

16. Method of diagnosing prediabetic forms of insulin-dependent diabetes mellitus (IDDM) in an individual that does not exhibit clinical symptoms of IDDM, comprising assaying for anti-sulphatide antibody in a sample with a complex of a water soluble polymer containing hydrophobic regions and sulphatide, wherein a detected elevated level of the antibody compared to the healthy population is taken as a marker for a prediabetic state of the individual.

* * * * *